(12) United States Patent
Mantzilas et al.

(10) Patent No.: US 10,702,613 B2
(45) Date of Patent: Jul. 7, 2020

(54) ISOTOPE PREPARATION METHOD

(71) Applicant: BAYER AS, Oslo (NO)

(72) Inventors: Dimitrios Mantzilas, Sørumsand (NO); Jan Roger Karlson, Oslo (NO); Judit Tjelmeland Østby, Kråkstad (NO); Janne Olsen Frenvik, Oslo (NO)

(73) Assignee: BAYER AS, Oslo (NO)

( * ) Notice: Subject to any disclaimer, the term of this patent is extended or adjusted under 35 U.S.C. 154(b) by 0 days.

(21) Appl. No.: 16/066,600

(22) PCT Filed: Dec. 29, 2016

(86) PCT No.: PCT/EP2016/082837
§ 371 (c)(1),
(2) Date: Jun. 27, 2018

(87) PCT Pub. No.: WO2017/118592
PCT Pub. Date: Jul. 13, 2017

(65) Prior Publication Data
US 2019/0015530 A1    Jan. 17, 2019

(30) Foreign Application Priority Data
Jan. 5, 2016 (GB) .................................. 1600153.9

(51) Int. Cl.
| | | |
|---|---|---|
| *A61K 51/04* | (2006.01) | |
| *A61K 51/10* | (2006.01) | |
| *B01D 15/36* | (2006.01) | |
| *B01J 41/05* | (2017.01) | |
| *A61K 51/12* | (2006.01) | |
| *A61K 51/06* | (2006.01) | |

(52) U.S. Cl.
CPC ...... *A61K 51/0474* (2013.01); *A61K 51/0478* (2013.01); *A61K 51/065* (2013.01); *A61K 51/1093* (2013.01); *A61K 51/1282* (2013.01); *B01D 15/363* (2013.01); *B01J 41/05* (2017.01)

(58) Field of Classification Search
CPC .................................................... A61K 51/00
See application file for complete search history.

(56) References Cited

U.S. PATENT DOCUMENTS

| | | | | |
|---|---|---|---|---|
| 4,390,517 | A * | 6/1983 | O'Brien | ................. A61K 51/06 422/503 |
| 5,809,394 | A | 9/1998 | Bray et al. | |
| 2004/0208821 | A1 | 10/2004 | Larsen et al. | |
| 2006/0228297 | A1* | 10/2006 | Larsen | ............... A61K 51/1027 424/1.11 |
| 2013/0183235 | A1* | 7/2013 | Ramdahl | ............ A61K 51/0478 424/1.53 |

FOREIGN PATENT DOCUMENTS

EP    2 564 396    5/2015

OTHER PUBLICATIONS

International Search Report for PCT/EP2016/082837, dated Mar. 21, 2017, 3 pages.
Written Opinion of the ISA for PCT/EP2016/082837, dated Mar. 21, 2017, 6 pages.

\* cited by examiner

*Primary Examiner* — Michael G. Hartley
*Assistant Examiner* — Jagadishwar R Samala
(74) *Attorney, Agent, or Firm* — Morrison & Foerster LLP

(57) ABSTRACT

The present invention provides a method for the purification of $^{227}$Th from a mixture comprising $^{227}$Th and $^{223}$Ra, said method comprising: i) preparing a first solution comprising a mixture of $^{227}$Th and $^{223}$Ra ions dissolved in an aqueous solution of first mineral acid; ii) loading said first solution onto a strong base anion exchange resin; iii) eluting $^{223}$Ra from said strong base anion exchange resin using a second mineral acid in an aqueous solution; iv) optionally rinsing said strong base anion exchange resin using a first aqueous medium; v) eluting $^{227}$Th from said strong base anion exchange resin using a third mineral acid in an aqueous solution whereby to generate a second solution comprising $^{227}$Th. The invention further provides a purified $^{227}$Th solution, a corresponding pharmaceutical formulation and methods of treatment of neoplastic disease.

24 Claims, 3 Drawing Sheets

Figure 1 – In-growth of radium-223 upon decay of thorium-227

Figure 2 – Manufacturing process and process control

ISOTOPE PREPARATION METHOD

This application is the U.S. national phase of International Application No. PCT/EP2016/082837 filed Dec. 29, 2016, which designated the U.S. and claims priority to GB Patent Application No. 1600153.9 filed Jan. 5, 2016, the entire contents of each of which are hereby incorporated by reference.

FIELD OF THE INVENTION

The present invention relates to the purification of thorium-227 ($^{227}$Th) for pharmaceutical use. In particular, the present invention relates to methods of purification of thorium-227 shortly prior to use in pharmaceutical administration to human subjects.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of many other diseases, especially immunological, hyperplastic and/or other neoplastic diseases.

The most common methods of selective treatment are currently surgery, chemotherapy and external beam irradiation. Targeted endo-radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been a recent surge in interest in the use of alpha-emitting radionuclides in therapy because of their potential for more specific cell killing. One alpha-emitting nuclide in particular, radium-223 ($^{223}$Ra) has proven remarkably effective, particularly for the treatment of diseases associated with the bone and bone-surface. Additional alpha-emitters are also being actively investigated and one isotope of particular interest is the alpha-emitter thorium-227.

The radiation range of typical alpha emitters in physiological surroundings is generally less than 100 micrometers, the equivalent of only a few cell diameters. This makes these nuclei well suited for the treatment of tumours, including micrometastases, because little of the radiated energy will pass beyond the target cells and thus damage to surrounding healthy tissue might be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). These properties explain the exceptional cytotoxicity of alpha emitting radionuclides and also impose stringent demands on the level of purity required where an isotope is to be administered internally. This is especially the case where any contaminants may also be alpha-emitters, and most particularly where long half-life alpha emitters may be present, since these can potentially be retained in the body and cause significant damage over an extended period of time. Whether long or short half-life, however, radiochemical purity should be as high as reasonably feasible and contamination with non-targeted radionuclides should be minimised.

The radioactive decay chain from $^{227}$Ac, generates $^{227}$Th and then leads to $^{223}$Ra and further radioactive isotopes. The first three isotopes in this chain are shown in FIG. 3. The table shows the element, molecular weight (Mw), decay mode (mode) and Half-life (in years (y) or days (d)) for $^{227}$Th and the isotopes preceding and following it. Preparation of $^{227}$Th can begin from $^{227}$Ac, which is itself found only in traces in uranium ores, being part of the natural decay chain originating at $^{235}$U. One ton of uranium ore contains about a tenth of a gram of actinium and thus although $^{227}$Ac is found naturally, it is more commonly made by the neutron irradiation of $^{226}$Ra in a nuclear reactor.

It can be seen in FIG. 3 that $^{227}$Ac, with a half-life of over 20 years, is a very dangerous potential contaminant with regard to preparing $^{227}$Th from the decay chain for pharmaceutical use. Even once the $^{227}$Ac is removed or reduced to a safe level, however, $^{227}$Th will continue to decay to $^{223}$Ra with a half-life of just under 19 days. Since $^{223}$Ra is an alkaline earth metal it will not easily be coordinated by ligands designed for thorium or other actinides. This $^{223}$Ra then forms the beginning of a potentially uncontrolled (untargeted) decay chain including 4 alpha-decays and 2 beta-decays before reaching stable $^{207}$Pb. These are illustrated in the table below:

| Nuclide | $^{227}$Th | $^{223}$Ra | $^{219}$Rn | $^{215}$Po | $^{211}$Pb | $^{211}$Bi | $^{207}$Tl | $^{207}$Pb |
| --- | --- | --- | --- | --- | --- | --- | --- | --- |
| ½-life | 18.7 d | 11.4 d | 4.0 s | 1.8 ms | 36.1 m | 2.2 m | 4.8 m | stable |
| α-energy/MeV | 6.15 | 5.64 | 6.75 | 7.39 | | 6.55 | | |
| β-energy (max)/MeV | | | | | 1.37 | | 1.42 | |
| Energy % | 17.5 | 16.0 | 19.1 | 21.0 | 3.9 | 18.6 | 4.0 | |

It is evident from the above two decay tables that $^{223}$Ra cannot be entirely eliminated from any preparation of $^{227}$Th because the latter will constantly be decaying and generating the former. It is clear, however, that more than 25 MeV in radiated energy will be released from the decay of each $^{223}$Ra nucleus administered to a patient, before that nucleus reaches a stable isotope. It is also probable that such $^{223}$Ra will not be bound and targeted by the systems of chelation and specific binding designed to transport $^{227}$Th to its site of action, due to the differing chemical nature of the two elements. Therefore, for the purpose of targeted cell killing, maximising the therapeutic effect and minimising side-effects, it is important that as much $^{223}$Ra as realistically possible should be removed from any $^{227}$Th preparation prior to administration.

Separation of $^{227}$Th from $^{223}$Ra could be carried out quickly and conveniently in a radiological laboratory such as at the site of generation by decay of $^{227}$Ac. However, this would not always be possible and may not achieve the desired result effectively because the resulting purified $^{227}$Th must then be transported to the site of administration. If this site of use is remote from the site of origin of the $^{227}$Th then a further build-up of $^{223}$Ra will occur during storage and transport.

In view of the above, it would be a considerable advantage to provide a robust and effective method of purifying $^{227}$Th from contaminant $^{223}$Ra which could be carried out at a location, such as a centralized location, from which the purified $^{227}$Th can reach the site of administration significantly more quickly than the half-life of the isotope. Where the purified isotope will be stored from some time (e.g. 12 to 60 hours) then the method should preferably provide a very high degree of removal of $^{223}$Ra so that only radium caused by unavoidable in-growth is administered to the subject without any significant increase due to residual impurity. Alternatively, purification may take place at or close to the point-of-care, at or shortly before the time of administration utilising a simple method that would not require extensive training and experience to carry out. It would be a further advantage if this method could be implemented with a simple group of reagents and items of apparatus, which could be supplied for such a contemporaneous preparation, optionally in the form of a kit. In either embodiment, the method should be robust, reliable and effective, since the resulting purified $^{227}$Th may be used directly in pharmaceutical preparation.

Previously known preparations for $^{227}$Th have generally been for laboratory use and/or not tested for purity to pharmaceutical standards. In WO2004/091668, for example, $^{227}$Th was prepared by anion exchange from a single column and used for experimental purposes without validation of the purity. The primary aim of separation in most preparative methods for $^{227}$Th has been the removal of the long-lived $^{227}$Ac parent isotope. Methods have not previously been devised or optimised for removal of $^{223}$Ra which has grown-in in a $^{227}$Th sample previously purified from $^{227}$Ac. Furthermore, there are few, if any, documented methods for preparing pharmaceutical standard $^{227}$Th that conform to or are suitable for conforming to Good Manufacturing Practice (GMP) principles. It would be an advantage to provide an effective and reliable method that could readily be validated and documented in accordance with GMP working practices.

Brief Description of the Invention

The present inventors have now established that a quick and simple purification procedure may be used to remove $^{223}$Ra and its daughter isotopes from a preparation of $^{227}$Th using a single strong base anion exchange resin. In this way, a $^{227}$Th solution of very high radiochemical purity may be produced while providing a number of desirable advantages in the method.

In a first aspect, the present invention therefore provides a method for the purification of $^{227}$Th from a mixture comprising $^{227}$Th and $^{223}$Ra, said method comprising:
  i) preparing a first solution comprising a mixture of $^{227}$Th and $^{223}$Ra ions dissolved in an aqueous solution of first mineral acid;
  ii) loading said first solution onto a strong base anion exchange resin;
  iii) eluting $^{223}$Ra from said strong base anion exchange resin using a second mineral acid in an aqueous solution;
  iv) optionally rinsings said strong base anion exchange resin using a first aqueous medium;
  v) eluting $^{227}$Th from said strong base anion exchange resin using a third mineral acid in an aqueous solution whereby to generate a second solution comprising 227Th.

The process will optionally and preferably also include at least one of the following further steps, each generally conducted after steps i) to v) above:
  vi) assaying for the $^{227}$Th content of said second solution;
  vii) evaporating the liquid from said second solution;
  viii) forming at least one radiopharmaceutical from at least a portion of the $^{227}$Th contained in said second solution;
  ix) sterile filtering said radiopharmaceutical.

In a further aspect, the present invention provides a solution or other sample of $^{227}$Th comprising less than 10 KBq, preferably less than 5 KBq (e.g. less than 2 KBq) $^{223}$Ra per 1 MBq $^{227}$Th. Such a solution is optionally formed or formable by any of the methods herein described, and is preferably formed or formable by the preferred methods herein described. Correspondingly, the methods of the invention are preferably for the formation of a solution of $^{227}$Th comprising less than 10 KBq, preferably less than 5 KBq $^{223}$Ra per 1 MBq $^{227}$Th. A corresponding pharmaceutical preparation is also provided, which may be sterile and may comprise at least one complexing agent (especially for $^{227}$Th), at least one targeting agent (e.g. conjugated to said complexing agent), and optionally at least one pharmaceutically acceptable carrier or diluent.

In a still further aspect, the invention also provides a kit (typically a kit for carrying out a method of the invention) comprising a mixture of $^{227}$Th and $^{223}$Ra, a first mineral acid, a strong base anion exchange resin, a second mineral acid, a first aqueous medium, and a third mineral acid. The kit may further comprise container closures, adapters, syringes, needles, evaporation tubing kit and/or a sterile filter. The mixture of $^{227}$Th and $^{223}$Ra (as with the first solution in other aspects of the invention) will typically also comprise further $^{223}$Ra daughter products. Such a mixture may be the result of radioactive decay of purified or partially purified $^{227}$Th during storage and/transportation.

DETAILED DESCRIPTION OF THE INVENTION

Pharmaceuticals of all types must routinely be produced to a very high standard of purity and a very high confidence that standards (e.g. of purity and sterility) have been met. Administration of an alpha-emitting radionuclide to the body of a subject requires all of these considerations but additionally adds a need for high radiochemical purity. Purification from long-lived precursor isotopes is one key aspect of radiochemical purity but this can typically be accomplished in a specialist radiochemical laboratory or factory where complex methods and handling procedures can be utilised.

A further level of radiochemical purification may be necessary, however, in the event that the radionuclide of interest decays to other radioactive isotopes. The generation of radioactive daughter isotopes may contribute significantly to the toxicity of endo-radionuclide therapy and can be dose-limiting. In the case of $^{227}$Th, the daughter isotope is radium, an alkaline earth metal while the parent is a transition metal of the actinide series. This means that any chelation or complexation which may have been suitable for binding thorium will probably not be chemically suitable for retaining the daughter radium. Alpha decay additionally imparts a very significant "recoil" energy onto the daughter nucleus as a result of conservation of momentum following ejection of an alpha particle at very high speeds. This recoil carries many times more energy than a covalent bond or coordinating interaction and will inevitably shunt the daughter nucleus out of the immediate environment of the original parent isotope. This combination of recoil energy and lack of chelation for the daughter isotope results in uncontrolled release of the daughter isotope following most alpha-decays.

Since the presence of $^{223}$Ra and its daughters generated by $^{227}$Th decay may be dose limiting, it is important that no unnecessary $^{223}$Ra is administered to the subject to further limit the acceptable therapeutic dose of $^{227}$Th or to exaggerate the side effects.

The present invention has been developed in view of the inevitable in-growth of $^{223}$Ra into a $^{227}$Th sample and the desire to minimise that $^{223}$Ra delivered to the subject, as far as reasonably possible. Since $^{223}$Ra will initially grow in at a rate of around 0.2% of the total activity per hour, the method must be carried out within a few hours before administration (e.g. within 72 hours or within 48 hours) in order to minimise the unnecessary dose. A period of 48 hours between preparation and administration would, for example, result in around 12% decay to radium and thus an additional 1% residual radium would increase the radium administered by around 8%. Correspondingly, if the $^{227}$Th can be used within a short time following preparation then the method should preferably provide $^{227}$Th with around 99% (e.g. 95% to 99.9%) radiochemical purity with respect to $^{223}$Ra (at the time of purification). Higher purity may be inefficient since ingrowth before use will undo any benefits of a more stringent purification method while lower purity (say less than 90% or less than 95% radiochemical purity) is undesirable because the dose of $^{223}$Ra (and thus toxicity) could reasonably be further limited while allowing for a realistic administration time.

In one embodiment, the mixtures of $^{227}$Th and $^{223}$Ra for use in the present invention will contain no significant amount of radioactive isotopes that are not in the decay chain beginning at $^{227}$Th. In particular, the mixtures of $^{227}$Th and $^{223}$Ra for use in any of the aspects of the present invention will preferably comprise less than 20 Bq $^{227}$Ac per 100 MBq $^{227}$Th, preferably less than 5 Bq $^{227}$Ac per 100 MBq $^{227}$Th.

The present invention provides a method for the production of $^{227}$Th at a purity suitable for use in endo-radionuclide therapy. A number of preferred features of the system are indicated below, each of which may be used in combination with any other feature where technically viable, unless indicated otherwise.

The methods and all corresponding embodiments of the invention will preferably be carried out on a commercial or clinical scale and thus will be capable and suitable for use at this scale while maintaining all of the other characteristics described herein as appropriate (such as radionuclear purity, etc). A commercial scale will typically be a scale greater than that required for the treatment of a single subject, and may be, for example, the purification of more than 2, preferably more than 5 and most preferably more than 20 typical doses of $^{227}$Th. Evidently, a typical dose will depend upon the application, but anticipated typical dose may be from 0.1 to 20 MBq, preferably 0.5 to 12 MBq, most preferably around 1 to 10 MBq. Purification may take place in batches of, for example 20 to 500 MBq, preferably 50 to 200 MBq, especially around 100 MBq. Purification of a single dose may, however, be undertaken, particularly where the purification is carried out immediately prior at administration (e.g. within 2 hours, preferably within 1 hour of administration).

Step i) of the method of the invention relates to solution comprising $^{227}$Th and $^{223}$Ra (and will commonly also comprise $^{223}$Ra daughter isotopes—see those tabulated above). Such a mixture will inherently form by the gradual decay of a sample of $^{227}$Th, but for use in the invention will preferably also have one or more of the following features, either individually or in any viable combination:
a) The $^{227}$Th radioactivity may be at least 0.1 MBq (e.g. 0.1 MBq to 500 MBq), preferably at least 1.4 MBq, more preferably at least 7 MBq and most preferably at least 20 MBq (e.g. 20 to 200 or around 100 MBq);
b) The solution may be formed in an aqueous solution of a first mineral acid;
c) The solution may have a volume of no more than 20 ml (e.g. 0.1 to 10 ml), preferably no more than 3 ml, more preferably no more than 2.5 ml.
d) The first mineral acid may be an acid selected from $H_2SO_4$ or $HNO_3$ preferably $HNO_3$.
e) The first mineral acid may be used at a concentration of 1 to 16 M, such as 3 to 10 M or 5 to 9 M, preferably 7 to 8.5 M (e.g. around 8M), particularly where the first mineral acid is $HNO_3$. ***

Step ii) of the method of the invention relates to the loading of the first solution onto a strong base anion exchange resin. This step and the entities referred to therein may have the following preferable features, either individually or in any viable combination, and optionally in any viable combination with any of the features of the other steps as described herein:
a) The strong base anion exchange resin may be a polystyrene/divinyl benzene copolymer based resin, preferably containing 1-95%; divinyl benzene
b) The strong base anion exchange resin may be an R—N$^+$Me$_3$ type (type I) resin or an R—N$^+$Me$_2$CH$_2$CH$_2$OH (Type II) resin, preferably a type I resin;
c) The strong base anion exchange resin may have an exchange capacity of 0.2 to 5 meq/ml, preferably 0.6 to 3 meq/ml, most preferably 0.9 to 1.5 meq/ml (e.g. around 1.0 meq/ml);
d) The strong base anion exchange resin may have a particle size grading of 10 to 800 mesh, preferably 50 to 600 mesh, more preferably 100 to 500 mesh (e.g. around 200 to 400 mesh).
e) The strong base anion exchange resin may be used in the form of a column.
f) The volume of resin used (e.g. when packed in a column) may be 1 ml or less, (e.g. 0.01 to 1 ml), preferably 0.5 ml or less.
g) The strong base anion exchange resin may be DOWEX 1X8 (e.g. DOWEX AG 1X8) or equivalent resin with a 200-400 mesh size.
h) The strong base anion exchange resin may be pre-equilibrated with a mineral acid. This may be the same as the first mineral acid as described herein.

Step iii) of the method of the invention relates to eluting $^{223}$Ra (and preferably also at least one $^{223}$Ra daughter product) from the strong base anion exchange resin using a second mineral acid in aqueous solution. This step and the entities referred to therein may have the following preferable features, either individually or in any viable combination, and optionally in any viable combination with any of the features of the other steps as described herein:
a) The second mineral acid may be an acid selected from $H_2SO_4$ or $HNO_3$ preferably $HNO_3$.
b) The second mineral acid may be used at a concentration of 1 to 16 M, such as 3 to 10 M or 5 to 9 M, preferably 7 to 8.5 M (e.g. around 8M), particularly where the first mineral acid is $HNO_3$.
c) The second mineral acid in aqueous solution may be the same as the first mineral acid in aqueous solution.
d) The aqueous solution may be free or substantially free of any alcohol. In particular, the aqueous solution may contain less than 0.1% (e.g. 0 to 0.1%) of any alcohol selected from methanol, ethanol and isopropanol, particularly methanol;
e) The $^{223}$Ra (and optionally at least one daughter isotope) may be eluted from said strong base anion exchange resin using 1 to 200 column volumes of the second mineral acid in aqueous solution. Preferably the amount will be 5 to 20 column volumes (e.g. around 7 to 11 column volumes).

Step iv) of the method of the invention relates to the optional step of rinsing said strong base anion exchange resin using a first aqueous medium. This step and the entities referred to therein may have the following preferable features, either individually or in any viable combination, and optionally in any viable combination with any of the features of the other steps as described herein:
a) The first aqueous medium may be water, such as distilled water, deionised water or water for injections.
b) The first aqueous medium may contain said second mineral acid, preferably at a concentration lower than used in step v).
c) The first aqueous medium may be used in an amount of 1 to 200 column volumes.

Step v) of the method of the invention relates to eluting $^{227}$Th from said strong base anion exchange resin using a third mineral acid in an aqueous solution whereby to generate a second solution comprising $^{227}$Th. This step and the entities referred to therein may have the following preferable features, either individually or in any viable combination, and optionally in any viable combination with any of the features of the other steps as described herein:
a) The third mineral acid may be an acid selected from $H_2SO_4$ and HCl, preferably HCl.
b) The third mineral acid may be used at a concentration of 0.1 to 12M, preferably 0.5 to 6M, more preferably 2 to 4M, most preferably around 3M. This applies particularly where the second mineral acid is HCl.
c) The second $^{227}$Th solution may be eluted from said strong base anion exchange resin using 1 to 200 column volumes of the second mineral acid in aqueous solution. Preferably the amount will be 5 to 20 column volumes (e.g. around 7 to 11 column volumes).
d) The aqueous solution may be free or substantially free of other solvents such as alcoholic solvents.
e) The second $^{227}$Th solution will preferably have a contamination level of no more than 10 (e.g. 1 to 10) kBq $^{223}$Ra per 1 MBq $^{227}$Th, more preferably no more than 5 kBq $^{223}$Ra per 1 MBq 227Th.

The steps ii) to iv) of loading the $^{227}$Th and $^{223}$Ra mixture onto the base anion exchange resin, eluting a mixture of said $^{227}$Th and $^{223}$Ra solution may provide a separation ratio of $^{227}$Th to $^{223}$Ra of at least 50:1 (e.g. 50:1 to 500:1), preferably at least 100:1, more preferably at least 200:1.

g) The $^{227}$Th may be eluted from said strong base anion exchange resin in uncomplexed form, such as in the form of a sample salt in solution (e.g. as the salt of the third mineral acid).
h) Optionally, the use of complexing agents such as DTPA may be avoided, and in one embodiment all solutions used in steps ii to iv) are substantially free of complexing agents, such as DTPA.

The methods of the present invention may comprise a number of optional steps, each of which may be present or absent independently so far as technically possible.

Step vi) of the method of the invention relates to optionally assaying for the $^{227}$Th content of the second solution. This step and the entities referred to therein may have the following preferable features, either individually or in any viable combination, and optionally in any viable combination with any of the features of the other steps as described herein:
a) The assay calculation of thorium-227 may be performed using a dose calibrator, preferably a dose calibrator with an established dial setting for thorium-227.

Step vii) of the method of the invention relates to the optional step of evaporating the liquid from said second solution. This step may be desirable where the final pharmaceutical composition has a low volume or does not comprise as much of the third mineral acid or its salts as is present in the second solution. Typically this method will be most effective when the third mineral acid is an acid that can be removed by evaporation, such as a hydrohalic acid (e.g. HCl). This step and the entities referred to therein may have the following preferable features, either individually or in any viable combination, and optionally in any viable combination with any of the features of the other steps as described herein:
a) The third mineral acid may be an acid selected from $H_2SO_4$ and HCl, preferably HCl.
b) The evaporation may be conducted under reduced pressure (e.g. 1 to 500 mbar).
c) The evaporation may be conducted at elevated temperature (e.g. 50 to 200° C., preferably 80 to 110° C.);

Step viii) of the method of the invention relates to the optional step of forming at least one radiopharmaceutical from at least a portion of the $^{227}$Th purified by means of steps i) to v). This step and the entities referred to therein may have the following preferable features, either individually or in any viable combination, and optionally in any viable combination with any of the features of the other steps as described herein. Furthermore, all of the features of the radiopharmaceutical indicated herein form preferred features of the pharmaceutical aspect of the present invention, particularly where that pharmaceutical is formed or formable by a method of the invention:
a) The portion of the $^{227}$Th contained in said second sample (purified by means of steps i) to v)) may be 0.1 MBq to 100 MBq, preferably 1 to 10 MBq.
b) The radiopharmaceutical may comprise at least one complexing agent.
c) The complexing agent may be an octadentate ligand.
d) The complexing agent may be a hydroxypyridinone such as 3,2-hydroxypyridinone (2.3-HOPO) ligand, preferably an octadentate 3,2-HOPO.
e) The radiopharmaceutical may comprise a targeting moiety.
f) The targeting moiety may be an anntibody, antibody construct, antibody fragment (e.g. FAB or F(AB)'2 fragment) or any fragment comprising at least one antigen binding region(s).

g) The targeting moiety may be a small organic molecule binder, a receptor or receptor binder (e.g. a hormone, vitamin, folate or a folate analogue) a bisphosphonate or nano-particle.
h) The targeting moiety may have specificity for at least on disease-associated antigen such as a "cluster of differentiation" (CD) cell surface molecule (e.g. CD22, CD33, CD34, CD44, CD45, CD166 etc).
i) The targeting moiety may be linked to the complexing agent by a covalent linker whereby to form a targeting conjugate.
j) The method of formation may comprise incubating the portion of the $^{227}$Th contained in said second sample with the targeting conjugate. Such incubation may be at a temperature below 50° C., preferably 20 to 40° C. Such incubation may be for a period of less than 2 hours, such as 1 minute to 60 minutes, most preferably 45 minuttes.

The radiopharmaceutical formed or formable in the various aspects of the present invention may be used in the treatment of any suitable disease, such as a neoplastic or hyperplastic disease including cancer (e.g. a carcinoma, sarcoma, melanoma, lymphoma, or leukemia). Such a use and the corresponding methods of treatment of a subject form further aspects of the invention. The invention will further provide for a method of administration of a radiopharmaceutical to a subject (e.g. one in need thereof) comprising forming said radiopharmaceutical by steps i) to v), viii) and optionally steps vi), vii) and ix) and injecting said radiopharmaceutical (e.g. by intravenous injection or injection directly to a specific tissue or site).

Step ix) of the method of the invention is an optional step comprising sterile filtering the pharmaceutical (especially that formed in step viii)). This step and the entities referred to therein may have the following preferable features, either individually or in any viable combination, and optionally in any viable combination with any of the features of the other steps as described herein:
a) The filtration may be through a suitable membrane, such as a 0.22 μm (or smaller) membrane.
b) The filtration may be by syringe through a suitable syringe filter.

In addition to the above steps, the methods of the invention and all corresponding aspects may comprise additional steps, for example to validate the purity of the $^{227}$Th for pharmaceutical purposes, to exchange counter-ions, concentrate or dilute the solution or to control factors such as pH and ionic strengths. Each of these steps thus forms an optional but preferable additional step in the various aspects of the present invention.

It is preferable that the methods of the present invention provide for a high yield of the $^{227}$Th product. This is not only because of the desire to avoid wastage or a valuable product but also because all lost radioactive material forms radioactive waste which must then be disposed of safely. Thus, in one embodiment, at least 50% (e.g. 50 to 90%) of the $^{227}$Th loaded in step ii) is eluted in step v). This will preferably be at least 60%, more preferably at least 65% and most preferably at least 68% yield or at least 70% yield.

In a corresponding aspect of the present invention, there is additionally provided pharmaceutical composition comprising the $^{227}$Th and optionally at least one pharmaceutically acceptable diluent. Such a pharmaceutical composition may comprise $^{227}$Th of a purity indicated herein (preferably complexed as described herein and conjugated to a targeting molecule as described herein), optionally formed or formable by the methods of the present invention. Suitable carriers and diluents including water for injection, pH adjusters and buffers, salts (e.g. NaCl) and other suitable materials will be well known to those of skill in the art.

The pharmaceutical composition will comprise the $^{227}$Th as described here, typically as an ion, such as the Th$^{4+}$ ion. Such compositions may comprise a simple salt of the $^{227}$Th of the invention but will more preferably comprise a complex of the $^{227}$Th of the invention with at least one ligand, such as an octadentate 3,2-hydroxypyridinone (3,2-HOPO) ligand. Suitable ligands are disclosed in WO2011/098611, which is hereby incorporated by reference, particularly with reference to formulae I to IX disclosed therein, which represent typical suitable HOPO ligands. Such ligands may be used in themselves or conjugated to at least one targeting moiety, such as an antibody. Antibodies, antibody constructs, fragments of antibodies (e.g. FAB or F(AB)'2 fragments or any fragment comprising at least one antigen binding region(s)), constructs of fragments (e.g. single chain antibodies) or a mixture thereof are particularly preferred. The pharmaceutical compositions of the invention may thus comprise Th$^{4+}$ ion of $^{227}$Th of pharmaceutical purity as disclosed herein, complexed to a conjugate of a 3,2-hydroxypyridinone (3,2-HOPO) ligand and at least one antibody, antibody fragment or antibody construct, plus optionally pharmaceutically acceptable carriers and/or diluents. The embodiments described herein with respect to the pharmaceutical composition will also form embodiments of the corresponding method where practicable and vice versa.

In one embodiment, the kit of the invention may comprise components needed for any of the methods of the present invention, optionally including any optional steps, such as steps vi) to ix) as described herein. Such components will have the features set out herein with respect to the corresponding steps, such as step viii).

Where the kit of the invention is suitable for carrying out the method of the present invention including optional step viii) (forming at least one radiopharmaceutical), the kit may include at least one of the following optional components:
a) A complexing agent, such as an octadentate ligand.
b) A hydroxypyridinone complexing agent such as 3,2-hydroxypyridinone (2.3-HOPO) ligand, preferably an octadentate 3,2-HOPO.
c) A targeting moiety, optionally and preferably conjugated or conjugatable to the complexing agent.
d) A targeting moiety selected from an anntibody, antibody construct, antibody fragment (e.g. FAB or F(AB)'2 fragment) or any fragment comprising at least one antigen binding region(s).
e) A targeting moiety selected from a small organic molecule binder, a receptor or receptor binder (e.g. a hormone, vitamin, folate or a folate analogue) a bisphosphonate or nano-particle.
f) A targeting moiety having specificity for at least one disease-associated antigen such as a "cluster of differentiation" (CD) cell surface molecule (e.g. CD22, CD33, CD34, CD44, CD45, CD166 etc).

As used herein, the term "comprising" is given an open meaning such that additional components may optionally be present (thus disclosing both "open" and "closed" forms). In contrast the term "consisting of" is given a closed meaning only, such that (to an effective, measurable and/or absolute degree), only those substances indicated (including any optional substances as appropriate) will be present. Correspondingly, a mixture or substance described as "consisting essentially of" will in essence consist of the stated components such that any additional components do not affect the essential behaviour to any significant extent. Such mixtures may, for example, contain less than 5% (e.g. 0 to 5%) of other components, preferably less than 1% and more preferably less than 0.25% of other components. Similarly, where a term is given as "substantially", "around", "about" or "approximately" a given value, this allows for the exact value given, and independently allows for a small variability, particularly where this does not affect the substance of the property described. Such variability may be, for example ±5% (e.g. ±0.001% to 5%), preferably ±1%, more preferably ±0.25%.

The invention will now be illustrated further by reference to the following non-limiting examples and the attached figures, in which.

EXAMPLES

Example 1—Batch Purification

Figure 1:
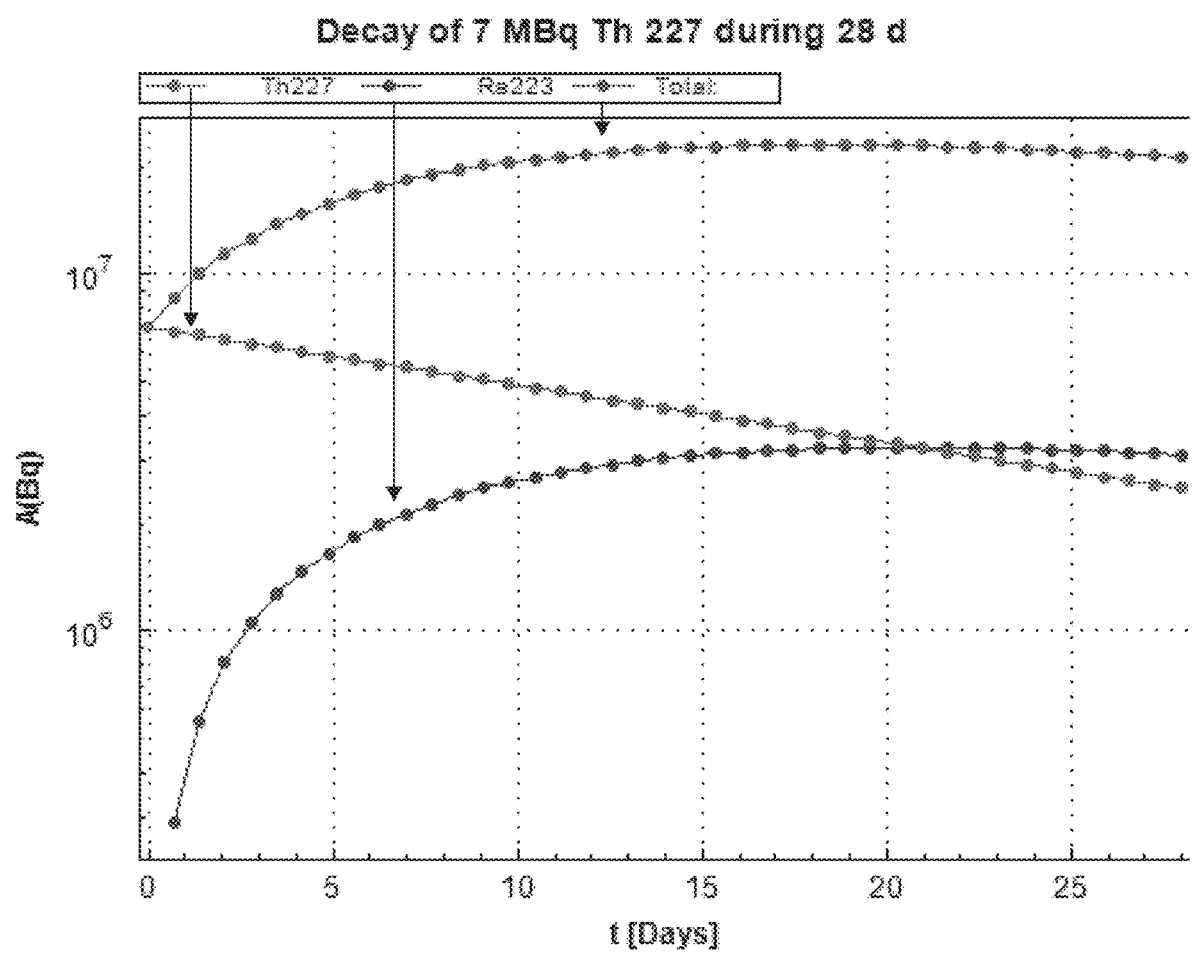
FIG. 1 Shows the decay of $^{227}$Th over time and the corresponding in-growth of $^{223}$Ra and daughter isotopes over 28 days.
Figure 2:
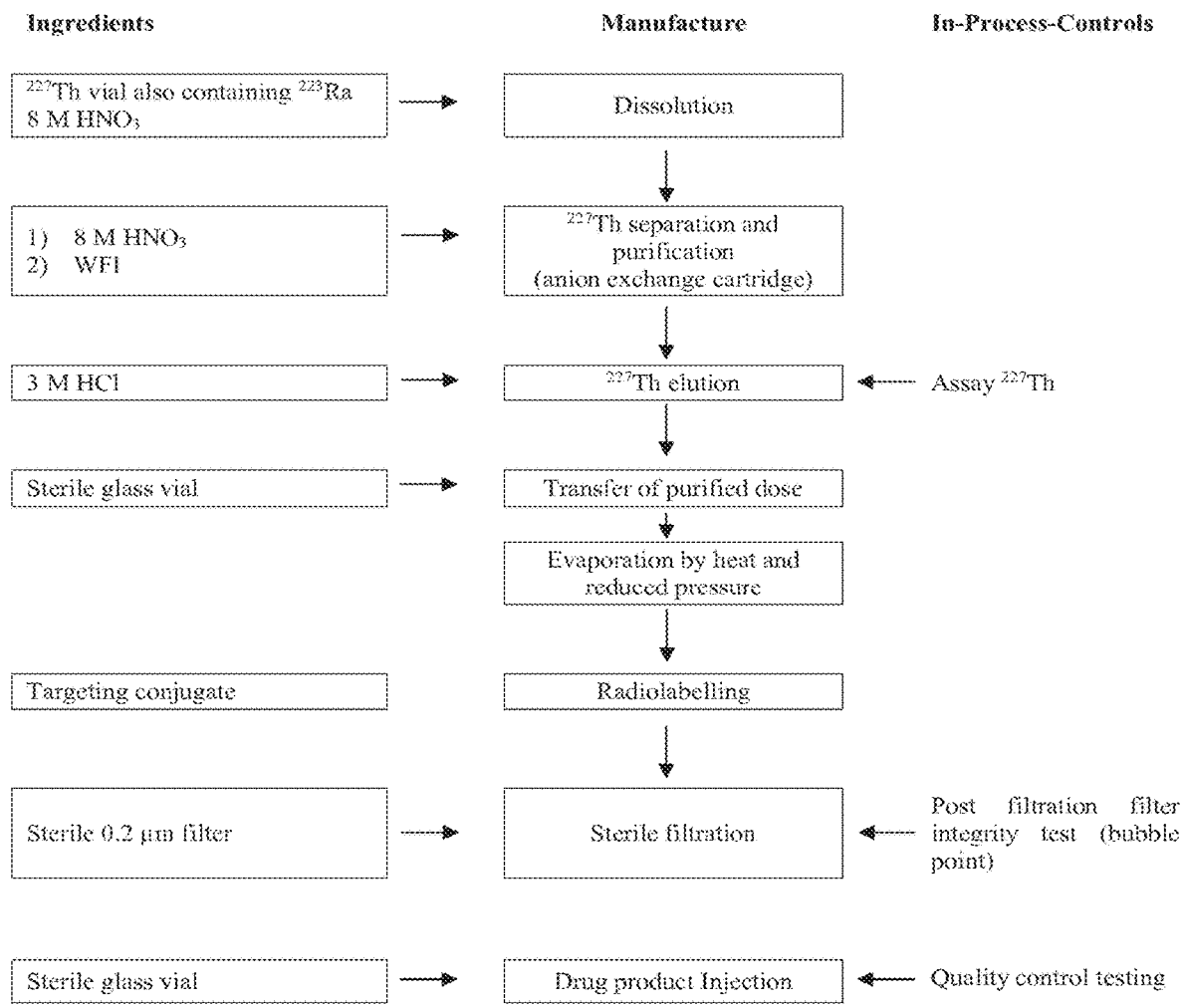
FIG. 2 Shows a typical manufacturing process and control, comprising an embodiment of the method of the present invention including several optional steps.
Figure 3:
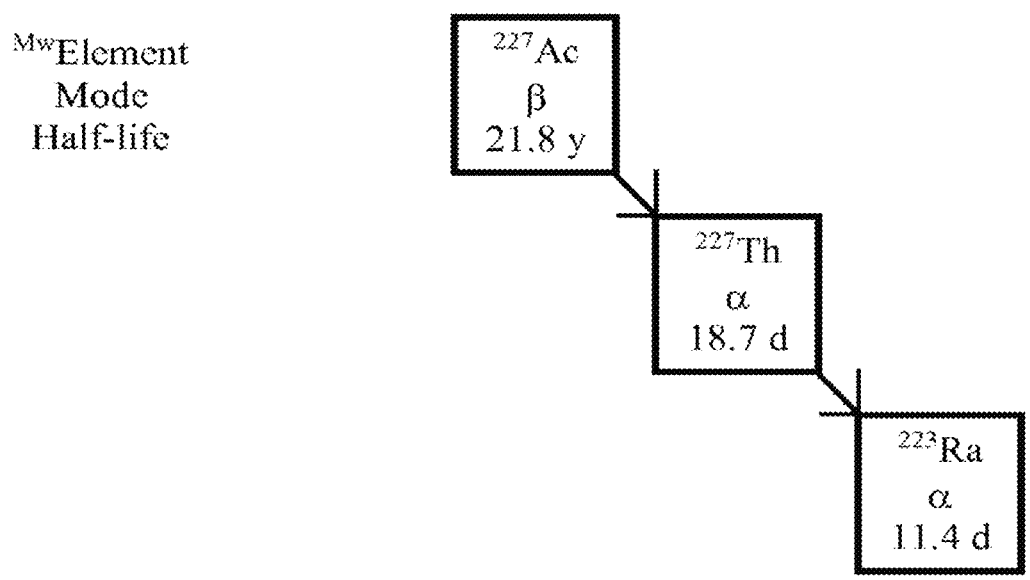
FIG. 3 Shows the decay chain for $^{227}$Ac.

Purification was carried out by the method indicated in FIG. 2.

| Test | Batch no. Technical batch 12 SUS | Batch no. Technical batch 14 SUS |
|---|---|---|
| Date of purification | Sep. 9th 2015 | Nov. 11th 2015 |
| Radionuclidic purity (RNP) Thorium-227 | 99.8% | 99.8% |
| Thorium-227 content in vial prior to purification | 100 MBq | 100 MBq |
| Separation ratio of $^{227}$Th to $^{223}$Ra | 500:1 | 500:1 |

The invention claimed is:

1. A method for purification of $^{227}$Th from a mixture comprising $^{227}$Th and $^{223}$Ra, said method comprising:
   i) preparing a first solution comprising a mixture of $^{227}$Th and $^{223}$Ra ions dissolved in an aqueous solution of a first mineral acid;
   ii) loading said first solution onto a strong base anion exchange resin;
   iii) eluting $^{223}$Ra from said strong base anion exchange resin using a second mineral acid in an aqueous solution;
   iv) optionally rinsing said strong base anion exchange resin using a first aqueous medium;
   v) eluting $^{227}$Th from said strong base anion exchange resin using a third mineral acid in an aqueous solution to generate a second solution comprising $^{227}$Th, wherein said second solution comprising $^{227}$Th has a contamination level of no more than 20 KBq $^{223}$Ra per 1 MBq $^{227}$Th;
   and at least one of steps vi)-viii):
   vi) assaying for $^{227}$Th content of said second solution;
   vii) evaporating the liquid from said second solution; and
   viii) forming at least one radiopharmaceutical from at least a portion of the $^{227}$Th contained in said second solution.

2. The method of claim 1, wherein at least 70% of the $^{227}$Th present in said first solution is present in said second solution.

3. The method of claim 1, wherein said method purifies sufficient $^{227}$Th for 1 to 20 doses.

4. The method of claim 1, wherein a $^{227}$Th radioactivity of at least 1 MBq is employed in step i).

5. The method of claim 1, wherein said strong base anion exchange resin is a polystyrene/divinyl benzene copolymer based resin.

6. The method of claim 1, wherein said strong base anion exchange resin and optionally a second strong base anion exchange resin are independently an R—N$^+$Me$_3$ (type I) resin or an R—N$^+$Me$_2$CH$_2$CH$_2$OH (type II) resin.

7. The method of claim 1, wherein said first mineral acid is an acid selected from the group consisting of H$_2$SO$_4$, HNO$_3$ and mixtures thereof.

8. The method of claim 1, wherein said first mineral acid is used at a concentration of 1 to 16 M.

9. The method of claim 1, wherein said second mineral acid is an acid selected from the group consisting of H$_2$SO$_4$, HNO$_3$ and mixtures thereof.

10. The method of claim 1, wherein said second mineral acid is used at a concentration of 1 to 16 M.

11. The method of claim 1, wherein said first aqueous medium is water for injections.

12. The method of claim 1, wherein said third mineral acid is an acid selected from the group consisting of H$_2$SO$_4$ and HCl.

13. The method of claim 1, wherein said third mineral acid is used at a concentration of 0.1 to 8 M.

14. The method of claim 1, wherein steps ii) to v) provide a separation ratio of $^{223}$Th to $^{223}$Ra of at least 10:1.

15. The method of claim 1, wherein step vii) comprises evaporation under reduced pressure, at elevated temperature, or under reduced pressure and at elevated temperature.

16. The method of claim 1, wherein step viii) comprises incubating the portion of the $^{227}$Th contained in said second solution with a targeting conjugate, wherein said incubating is at a temperature below 50° C. for a period of less than 2 hours.

17. The method of claim 16, wherein said radiopharmaceutical comprises a targeting conjugate formed from a targeting moiety linked to a complexing agent by a covalent linker.

18. The method of claim 17, wherein said complexing agent comprises an octadentate 3,2-HOPO ligand.

19. The method of claim 17, wherein said targeting moiety comprises an antibody, antibody construct or antibody fragment.

20. The method of claim 1, wherein when step viii) is carried out, said method further comprises:
   ix) sterile filtering said radiopharmaceutical.

21. The method of claim 5, wherein said polystyrene/divinyl benzene copolymer based resin contains 1-95% DVB.

22. The method of claim 7, wherein said first mineral acid comprises HNO$_3$.

23. The method of claim 9, wherein said second mineral acid comprises HNO$_3$.

24. The method of claim 12, wherein said third mineral acid is HCl.

* * * * *